United States Patent [19]

Weaver et al.

[11] 3,997,484

[45] Dec. 14, 1976

[54] HIGHLY-ABSORBENT STARCH-CONTAINING POLYMERIC COMPOSITIONS

[75] Inventors: Mary Ollidene Weaver, Peoria; Edward B. Bagley, Morton; George F. Fanta, Peoria; William M. Doane, Morton, all of Ill.

[73] Assignee: The United States of America as represented by the Secretary of Agriculture, Washington, D.C.

[22] Filed: Sept. 8, 1975

[21] Appl. No.: 611,461

Related U.S. Application Data

[62] Division of Ser. No. 456,911, April 3, 1974, Pat. No. 3,935,099.

[52] U.S. Cl. .................. 260/17.4 GC; 260/17.4 R; 260/17.4 CL; 260/17.4 ST
[51] Int. Cl.$^2$ .......................................... C08L 3/00
[58] Field of Search ............ 260/17.4 GC, 17.4 CL, 260/17.4 R, 17.4 ST

[56] References Cited

UNITED STATES PATENTS

| | | | |
|---|---|---|---|
| 3,288,707 | 11/1966 | Hurwitz et al. ...................... | 210/54 |
| 3,425,971 | 2/1969 | Gugliemelli et al. ............. | 260/17.4 |
| 3,661,815 | 5/1972 | Smith ............................... | 260/17.4 |
| 3,932,322 | 4/1976 | Duchane ......................... | 260/17.4 |

*Primary Examiner*—Edward M. Woodberry
*Attorney, Agent, or Firm*—M. Howard Silverstein; David G. McConnell

[57] ABSTRACT

Starch-containing polymer compositions are prepared which absorb amounts of water equaling up to more than 1000 times their own weight. The compositions find many applications including their incorporation into products such as disposable diapers, surgical pads and sheets, and paper towels.

15 Claims, No Drawings

HIGHLY-ABSORBENT STARCH-CONTAINING POLYMERIC COMPOSITIONS

This is a division of application Ser. No. 456,911 filed Apr. 3, 1974, and now U.S. Pat. No. 3,935,099.

BACKGROUND OF THE INVENTION

The invention relates to starch-graft copolymer compositions which absorb and retain under pressure large quantities of aqueous fluids and to their method of preparation. The invention further relates to various compositions and articles of manufacture which utilize the instant composition.

Crosslinked polymeric substances which possess the ability to absorb large quantities of fluids are known in the prior art. For example, U.S. Pat. No. 3,669,103 discloses that a variety of monomers may be polymerized to give copolymers and terpolymers which must be crosslinked in manners known in the polymer arts. One such copolymer contains carboxamide and carboxylate groups and is crosslinked by including a difunctional monomer such as N,N-methylenebisacrylamide into the polymerization solution. The crosslinking reaction is of critical importance. When the copolymers and terpolymers are not crosslinked, they are water soluble and have limited utility as absorbents.

U.S. Pat. No. 3,670,731 discloses the utility of particulate, water-insoluble, crosslinked polymeric compositions as absorbents in fabricated articles such as diapers, sanitary napkins, and the like.

It is an object of this invention to provide polymeric absorbent compositions which have the preparative ease and economic advantages inherent in starch graft copolymers and which will absorb aqueous fluids in quantities many times their own weight.

it is a further object of the invention to provide polymeric absorbent compositions which have not been subjected to normally used crosslinking compositions or procedures and yet are water-insoluble solids.

In accordance with the objects of the invention, we prepared aqueous fluid-absorbing compositions comprising water-insoluble alkali salts of saponified gelatinized-starch-polyacrylonitrile graft polymers containing gelatinized starch (GS) and saponified polyacrylonitrile (HPAN) in molar ratios of from about 1:1.5 to 1:9 GS:HPAN. The water-insoluble alkali salts of saponified gelatinized-starch-polyacrylonitrile graft polymers are further characterized as water-insoluble solids capable of absorbing in excess of 300 parts of water by weight per part of the water-insoluble solids.

Compositions comprising water-insoluble organic amine salts of the compositions described above were found to absorb aqueous fluids which contain organic components in major porportions.

Also in accordance with the objects of the invention, we discovered a method of preparing water-insoluble aqueous fluid-absorbing compositions comprising the following steps:

a. saponifying a gelatinized starch-polyacrylonitrile graft polymer (GS-PAN) in an aqueous slurry with an alkali in amounts such that the molar ratio of alkali to the acrylonitrile repeating unit of said GS-PAN is from about 0.1:1 to 7:1 to form a water-soluble saponified GS-PAN (water-soluble GS-HPAN; and b. optionally adjusting the pH of said water-soluble GS-HPAN to about 3 followed by isolating the resulting water-insoluble acid form of GS-HPAN, and readjusting the pH of said water-insoluble acid form of GS-HPAN to from about 4 to 12 to reform said water-soluble GS-HPAN; and c. drying said water-soluble GS-HPAN to a moisture level of from about 1 to 15% water by weight.

Incorporation of the instant compositions in disposable soft goods such as diapers, hospital bed pads, surgical pads and sheets, catamenial devices, and the like would greatly increase the fluid-absorbing capacity of the articles. Such increased absorbency of the disposable soft goods is important from both an economic and an ecological standpoint, since the higher absorbency permits the use of a smaller quantity of material to be disposed of by incineration or by discharge into sewage systems. The use of smaller quantities of GS-HPAN also decreases the amount of the synthetic polymers used in the application of the invention. Acrylonitrile is a petrochemical, and its decreased consumption increases the amount of petroleum that can be diverted to more urgently needed products. The instant compositions are also useful in agricultural applications for increasing water-holding capacity of soils which promotes more efficient germination of seeds and plant growth.

When the instant composition were applied as coatings onto substrates such as seeds, clay, starch, fibers, paper, or the like, a large increase in the water-holding capacity of the substrate was realized.

The organic amine salts of the invention, which absorb large amounts of aqueous-organic fluids, are useful in the formulation of jellied fuels, paint removers, and other formulations where it is desirable to have an organic solvent, containing a minimum amount of water, in an essentially solid form.

DETAILED DESCRIPTION OF THE INVENTION

In prior art methods of producing water-absorbing compositions, it was assumed that water-soluble products had to be rendered insoluble by crosslinking by the polymers, by saponifying in an aqueous-alcoholic medium, or by adjusting the pH so that the product was in an insoluble acid form. We were surprised, therefore, when we discovered a water-insoluble composition was formed by simply drying water-soluble saponified starch-polyacrylonitrile graft polymer containing starch that had been gelatinized prior to graft polymerization. We were further surprized when we found that the instant products had water absorptive capabilites which were from three to over 10 times greater than the best prior art starch graft compositions. The term "water-soluble composition" is herein defined to include apparently soluble or highly dispersed compositions.

Water-absorbing alkali salts of saponified starch-polyacrylonitrile graft polymers are disclosed in U.S. Pat. No. 3,661,815. Both the method of preparation and the resulting products disclosed therein differ from the method and compositions of the instant invention in several critical areas. It is specifically stated, for instance, in U.S. Pat. No. 3,661,815 that "carrying out the saponification in an alcohol-containing medium is an essential feature of (the) invention." Absorptive values in Table VII of U.S. Pat. No. 3,661,815 show that saponification in an alcohol-free medium results in a product having water-absorptive properties which are inferior to the product saponified in an alcohol-containing medium. It is also disclosed in U.S. Pat. No. 3,661,815 that pretreating starch in an aqueous slurry at 60° C. before grafting was beneficial to the product while pretreatment of starch at 65° C. was detrimental, and that "tapioca and potato starch required lower pretreatment temperatures, because of their lower gelatinization temperatures."

In contrast to the teachings disclosed in U.S. Pat. No. 3,661,815, we have found that in the instant method the presence of alcohol in the saponification medium is not only unnecessary, its use results in final products having significantly lower absorptive capabilities. Two portions of GS-PAN were saponified in the presence of alcohol and in the absence of alcohol in accordance with Examples 24–26 of U.S. Pat. No. 3,661,815, and the products, which were dried in vacuo at 110° C. for 16 hr., were tested for water and synthetic urine absorptivity. Aqueous-alcohol-KOH saponification resulted in a product which absorbed 31 g./g. (i.e., grams substance absorbed per gram absorbent composition) synthetic urine and 220 g./g. water. The aqueous-KOH saponification product absorbed 53 g./g. synthetic urine and 800 g./g. water. The reason that the aqueous-alcohol-KOH saponified product prepared in accordance with Examples 24–26, U.S. Pat. No. 3,661,815 (supra), had a higher absorptive value that is shown in Table VII, U.S. Pat. No. 3,661,815, for similar products is believed to lie in the fact that our starting material was GS-PAN (i.e., a starch-polyacrylonitrile graft polymer prepared from starch which had been pretreated in aqueous slurry at temperatures above the gelatinization temperature of the starch).

It is well known that starch in the granule state is insoluble in water at ambient temperatures. It is also known that when a water suspension of unmodified starch granules is heated the granules first slowly and reversibly take up water with limited swelling and then, at a definite temperature, typically about 70° C., the granules undergo irreversibly a sudden rapid swelling. As the temperature is increased beyond about 70° C., more starch molecules diffuse from the granules until, at a temperature range of about 80° to 100° C., the starch appears to become soluble. It is an essential and critical feature of the present invention that the graft copolymerization of acrylonitrile be carried out on starch that has been pretreated by methods known to those skilled in the art so as to render it soluble. We prefer to solubilize the starch by heating an aqueous suspension of starch to about 70° to 100° C. and holding the suspension at such temperatures for about 15 min. or longer.

We are aware, also, that U.S. Pat. No. 3,425,971 (cited as a reference in U.S. Pat. No. 3,661,815) discloses water-soluble alkali salts of (nongelatinized) starch-polyacrylonitrile graft polymers and the insoluble acid form therof which is resolubilized by adjusting the pH with alkali. The alkali salt products are used as thickeners and as such must be water soluble or completely water dispersible. In U.S. Pat. No. 3,425,971 (supra) as in U.S. Pat. No. 3,661,815 (supra), there is no teaching that simply gelatinizing the starch before graft polymerizing and drying the alkali salt graft polymer after saponification would give an insoluble product with such surprisingly different properties.

Starch-polyacrylonitrile graft copolymers are well known. Fanta, *Block and Graft Copolymerization*, R. J. Ceresa, ed., John Wiley and Sons, 1973, Chapter 1, has recently reviewed the various methods for making starch graft copolymers and the influence of such variables as type of initiator used, type of pretreatment of starch, kinds of polymerization media employed, amounts of monomer used, and the like on starch copolymer composition. The preferred monomer used to prepare the instant compositions is acrylonitrile (AN), but it is herein understood that methacrylonitrile (MAN) is equivalent to the acrylonitrile monomer specified in the claims. It is contemplated that, with a minimum of experimentation, those skilled in the art will find other monomers suitable for use in accordance with the invention and that monomers so found are also considered herein to be equivalent to acrylonitrile and methacrylonitrile. Preferred molar ratios of gelatinized starch to monomer range from about 1:1.5 to 1:9.

The preferred polymerization initiator is the ceric ammonium nitrate-nitric acid system used in the examples. However, other suitable initiator systems will be known to those skilled in the art (cf. Fanta, supra).

Saponification of GS-PAN is accomplished with an alkali defined herein as being the hydroxide of an alkali metal, preferably $Li^+$, $Na^+$, or $K^+$, or of $NH_4^+$. It is an essential feature of the instant invention that the saponification step be carried out in a manner such that a water-soluble product be obtained. Preferably, GS-PAN is contacted with an aqueous solution of alkali for from 1 to 3 hr. at a temperature of about 90°. Saponification apparently takes place only on the -PAN moiety of GS-PAN, converting nitrile groups to carboxamide and carboxylate groups to form the -HPAN moiety. During saponification, GS-PAN dissolves and forms a highly viscous solution of dispersion of GS-HPAN. Water-soluble GS-HPAN compositions were obtained from saponifications in which the molar ratio of alkali to the polyacrylonitrile repeating unit (i.e., alkali:AN) ranged from 0.1:1 to 7.2:1. Alkali:AN molar ratios of from 0.6:1 to 7.2:1 are preferred.

Compositions in accordance with the invention are prepared directly from the saponification reaction mixture without previous isolation of water-soluble GS-HPAN. However, higher absorptivities are obtained from GA-HPAN compositions which are purified before drying.

Isolation of water-soluble GS-HPAN is readily accomplished after completion of the saponification step by adjusting the pH of the reaction mixture by any suitable means to about 3, thereby precipitating the water-insoluble acid form of GS-HPAN. The water-insoluble precipitate is then isolated, washed, suspended in water, and the pH readjusted by any suitable means to a pH of from about 4 to 12, thereby reforming water-soluble GS-HPAN. Alternatively, the water-insoluble absorbent form of GS-HPAN can be prepared by packing a column with the acid form of GS-HPAN and allowing gaseous $NH_3$ to pass up the column for a period of time sufficient to form the ammonium salt.

The absorbent form of the polymer is prepared by simply drying the solution or dispersion obtained from the saponification step. Surprisingly, when a solution or dispersion containing the water-soluble GS-HPAN is cast into a film and subsequently dried by known routing methods including oven drying, drum drying, and air drying, the resulting dry films are insoluble and absorb up to about 300 times their weight in water forming clear, cohesive, self-supporting gel sheets. The dried films, which preferably contain from 1 to 15% moisture, can be ground or milled to give flakes or powders which have greatly increased surface areas over the films. The water-insoluble character of the product is retained by the flakes and the powders, and both forms display highly rapid uptake of fluids. The amount of fluid uptake by the flakes or powders is generally similar to amount of fluid uptake observed for the parent films. The absorbent polymer can be in the form of a mat or pad. Such forms result when the soluble form of the polymer is freeze or foam dried.

As an alternative to the drying procedures described above, the viscous mixture obtained after addition of alkali is diluted with a water-miscible organic solvent such as alcohol or acetone and the precipitated product isolated in powder form by filtration and drying.

Of particular importance is the fact that the dried GS-HPAN films are insoluble in all solvents despite the fact that no crosslinking reagents were added. Treatment with boiling water, boiling 1N potassium hydroxide, and boiling 1N hydrochloric acid failed to dissolve the instant films. The exact nature by which the polymer forms the insoluble films is not clearly understood. The insolubilization apparently takes place by some unknown mechanism when water solutions are dried at temperatures as low as room temperature or lower. The extremely mild conditions under which this insolubilization takes place are unique and unexpected. The insoluble and water-swollen graft copolymer was redispersed in water by subjecting it to high mechanical shear or to sonification. Mechanical shear was accomplished in a Waring blendor and a colloid mill. Surprisingly, if shearing has not been too extensive, this dispersion yields on drying, an absorbent, insoluble film which has properties similar to the original insoluble polymer. Even dispersions which have been subjected to the highest mechanical shear will form insoluble films if they are dried at room temperature and the dried films are then allowed to stand for from about 7 to 100 days at room temperature and high humidity, or if they are dried at 160° for from about 15 to 120 min. Insolubilization of these sheared polymers is accelerated by heat and gamma irradiation.

The absorbency of a film prepared in accordance with the invention was reduced from 600 to 100 g. water per gram of polymer by 3 megarads of gamma irradiation. Such control of film swellability can be utilized in the gel entrapment of enzymes, where a large initial swelling is desirable to allow the enzyme to penetrate into the film, but subsequent use of the film requires a lower degree of swelling to keep the enzyme trapped.

The commercial value of immobilized enzymes has been the subject of many reports in recent years. One of the more frequently used immobilization techniques has been physical entrapment. Hicks et al. [Anal. Chem. 38(6): 726–730 (1966)] describe a method of entrapping enzymes such as glucose oxidase in a polyacrylamide gel. As in most procedures which entrap enzymes within synthetic polymer matrices, it was necessary for the enzyme to be present during the polymerization of the acrylamide.

Enzymes have also been entrapped in starch gels [Bouman et al., Anal. Chem. 37: 1378 (1965)]. Enzymes were dissolved into a solution of starch and the mixture worked into a slab of polyurethane foam.

Water-insoluble GS-HPAN film was treated with an aqueous solution of glucoamylase, then treated with a solution of calcium chloride. The calcium chloride shrunk the fluid-swollen film sufficiently to entrap the enzyme, which remained active through five separate and consecutive reactions with starch. The amounts of enzyme, GS-HPAN, and calcium chloride would be different for each different enzyme, depending upon the enzyme's molecular size and desired activity. Therefore, the inventive method should not be limited to any particular enzyme or to any specific ratios of enzyme to water-absorbent GS-HPAN. Since the method simply involves the absorption of a solution of the desired enzyme by the water-absorbent film, it would be easy for one skilled in the art to perform a few experiments to determine the necessary amount of all components Any soluble mineral salt is suitable for shrinking the gel after it has absorbed the enzyme solution.

Immobilized amylase enzymes were prepared by two methods. One, an α-amylase, was covalently bonded to the instant water-absorbent compositions, and the other, a glucoamylase, was absorbed according to the method described above. It was surprising when we discovered that in neither immobilizing enzyme composition did the amylase degrade the starch moiety of the GS-HPAN, even though these enzymes are well-known degraders of starch.

The absorbent polymers of the present invention may be extended by mixing dispersions of water-soluble GS-HPAN with dispersions of inexpensive natural polymers, or their derivatives, and then drying the resulting mixtures Examples of such natural polymers are flour, guar, gelatin, starch, or dextrin.

An important application of dried water-insoluble GS-HPAN is the reduction of the water content of emulsions, suspensions, and dispersions. Milk containing 27.4% milk solids was treated with the water-absorbent composition in amounts such that the ratio of absorbent to water was about 1:100. The resulting filtrate, which was still a milk emulsion, contained 39.4% milk solids. It will be understood that milk solids include minerals, protein, and butterfat. Linseed oil-in-water emulsions containing 9.5% and 52.3% oil were concentrated to emulsions containing 12.3% and 57.9% oil, respectively, when treated with dried films of the absorbent compositions in amounts such that the ratios of absorbent to water were about 0.1:90 and 1:100, respectively. The numerous emulsions known to those skilled in the art will require varying amounts of the water-absorbent compositions of the instant invention to accomplish the desired amounts of concentration. However, optimum amounts of absorbent for each emulsion can be easily determined by a few simple trial experiments. Preferably, amounts of the instant absorbent composition to water contained in emulsions was from 0.1 to 1 part of absorbent to 100 parts of water (by weight).

Aqueous dispersions or suspensions such as sewage sludge can be beneficially treated by addition of the instant water-absorbent composition so that the use of settling ponds can be reduced or eliminated. Sewage sludge containing 3.9% solids was dewatered to the extent that the solids content was increased by 25% by the addition of 0.5 g. of absorbent to 100 ml. of sludge. When the same sewage sludge was treated with 1 part of absorbent to 100 ml. of sludge, the resulting fluid mass was too thick to pass through the 40-mesh sieve used to separate the gelled water-absorbing composition from concentrated sludge.

Although the fluid mass could be separated by other means, it is preferred that the instant compositions be added to the sludge at a rate of about 0.1 to 0.5 part absorbent per 100 ml. of water (by weight).

It was found that adding the water-absorbent composition to the sewage sludge at a rate of at least 2 parts absorbent per 100 parts water provided a crumbly-solid material which cannot be pumped but can be handled by mechanical means including shovels, scoops, end loaders, and conveyors. It can be carried in wheelbarrows and trucks, and can be dispersed on field by means of manure spreaders and the like. Theoretically, there is no upper limit to the amount of absorbent which can be combined with sewage sludge. However, for economic reasons, the preferred range of addition is from 2 to 10 parts absorbent per 100 parts water.

Thin films of water-insoluble GS-HPAN greatly increase the water-holding capacity of many substrates. Since prior art absorbent compositions require cross-linking reactions or saponifications in the presence of alcohol to make them insoluble, it would be very difficult to coat substrates with them in order to increase the water-absorptive abilities of the substrates. The instant absorptive compositions, on the other hand, can be easily obtained as coatings on any water-insoluble substrate by merely drying solution of water-soluble GS-HPAN while the solutions are in contact with the desired substrate. Examples of such substrates include silica, clay, animal litter or bedding, granular starch, cellulose fibers, cloth, and paper. The preferred amount of dry saponified starch-polyacrylonitrile is 0.5 to 3%, based on the dry weight of substrate.

Starch granules coated with water-absorbent GS-HPAN show a viscosity rise at a lower temperature than untreated starch when heated in water. Also, final viscosities after heating 90° C. are higher than that shown by untreated starch. In the manufacture of paper or mineral board, coated starches are retained better than untreated starch when added at the wet end along with a cationic retention aid.

Seeds may be coated with saponified starch-polyacrylonitrile and subsequently dried. Water content in the vicinity of the seed during germination would thus be maximized. Also, dry GS-HPAN, in powder or flake form, may be blended with soil. In an arid climate, such a blend will hold a higher percentage of water for longer periods than untreated soil. The instant compositions are also useful as soil conditioners. Silt-type soils are composed of fine particles which pack together to form almost impenetrable surfaces, increasing water runoff and greatly adding to erosion and pollution problems. Many polyelectrolyte materials have been used to aggregate soil particles so that the soil would allow water to penetrate, thereby minimizing water runoff.

Dispersions of water-soluble GS-HPAN were added to silt-loam soils in amounts of from 0.3 to 0.9 part GS-HPAN to 100 parts soil and the resulting soil allowed to dry, leaving a coating of water-absorbent compositions on the soil particles. These coated soils and uncoated control soils were then evaluated according to the soil conditioner testing method of R. M. Hedrick [J. Agr. Food Chem. 2(4): 182–185 (1954)]. Up to 96% of the soils coated with the instant compositions formed aggregates which would not pass a 20-mesh screen while 100% of untreated soil passed through 60-mesh screens.

By adding seeds to a dispersion or solution of saponified starch-polyacrylonitrile, casting and drying a film from the resulting mixture, the seeds are immobilized in a water-swellable film for use in gardening or farming.

Nutrients such as nitrates, lime, etc. can be added to the water-soluble GS-HPAN solution before casting the film, or they can be added as a solution to the seed containing water-absorbent film. Seeds thus immobilized can be planted in strips, or the film can be broken up and the seeds planted in a more conventional manner. Ground or powdered materials such as iron can be added to the slurry of seeds and water-soluble GS-HPAN before casting the seed-ladened film in order to give the immobilized seed sufficient weight to minimize its being washed away. The use of iron in the film allows handling by means of magnets.

The form of the polymer, which will absorb large quantities of aqueous-organic fluids where the organic material is the principle component, is prepared by first isolating the acid form from the saponification reaction mixture as described above and reacting it with a suitable organic amine in quantities such that the reaction mixture has a pH of from 5 to 11. The resulting thick solutions or dispersions of the organic-amine salts of GS-HPAN are then dried to yield insoluble films which will absorb organic fluids containing minimal amounts of water. Examples of suitable organic amines include primary amines such as methyl-, ethyl-, hexyl-, dodecyl-, benzyl-, chlorobenzyl-, and ethanolamines; secondary and tertiary analogs of the same; aniline; cyclohexylamine and pyridine. Other suitable amines will be known to those skilled in the art.

The following examples are intended only to further illustrate the invention which is defined by the claims.

All percentages mentioned herein are by weight unless otherwise specified.

EXAMPLES 1–8

A. Preparation of GS-HPAN

Stirred slurries consisting of 5 to 10% by weight starch in water were heated for 30 min. at the designated temperature, Table 1, and cooled under a nitrogen atmosphere to 27° C. To each stirred mixture was added 0.1 molar ceric ammonium nitrate solution in 1N nitric acid (see Table 1). After 10 min., acrylonitrile was added and the mixture stirred for 3 hr. at 35° C. The starch-polyacrylonitrile graft copolymer was isolated by filtration and dried, Table 1.

B. Preparation of water-insoluble acid form of GS-HPAN

The GS-PAN compositions from Examples 1A-8A were slurried in water and varying amounts of sodium or potassium hydroxide added, Table 2. The mixtures were stirred at 90° C. until the orange-red color, which formed on initial heating with alkali, had disappeared. The smooth, light yellow dispersions were diluted to 5% solids, cooled to room temperature, and sulfuric acid added to give a pH of 3.2. The water-insoluble acid form, which precipitated on acidification, was isolated by centrifugation and washed successively with water, 5:1 methanol-acetone, and acetone. The product was finally isolated by filtration and dried at 25° C., Table 2.

Table 1

| Example | Starch variety | GS, g. | AN, g. | H₂O, ml. | Ce⁺⁴, mmoles | Starch pretreat temp., °C | Reaction time, hr. | Yield, g. | GS:PAN mole ratio |
|---|---|---|---|---|---|---|---|---|---|
| 1A | Corn | 25.0 | 15.0 | 400 | 1.5 | 95 | 3 | 38.3 | 1:1.6 |
| 2A | Corn | 37.4 | 40.0 | 600 | 1.9 | 55 | 3 | 60.0 | 1:2.4 |
| 3A | Corn | 27.0 | 31.8 | 480 | 1.5 | 88 | 17 | 57.0 | 1:3.3 |
| 4A | Waxy sorghum | 27.0 | 31.8 | 480 | 1.5 | 88 | 17 | 57.0 | 1:3.3 |
| 5A | Wheat | 42.4 | 61.6 | 400 | 1.5 | 85 | 3 | 71.0 | 1:3.5 |
| 6A | Waxy corn | 42.0 | 61.5 | 400 | 1.5 | 90 | 3 | 87.0 | 1:3.8 |
| 7A | Wheat | 28.8 | 75.5 | 400 | 1.4 | 85 | 3 | 90.0 | 1:5.7 |
| 8A | Corn | 25.5 | 75.0 | 400 | 1.5 | 95 | 3 | 97.0 | 1:8.6 |

Table 2

| Example | GS-PAN (from Part A) Amount, g. | Conc. in H₂O, wt. % | Alkali | Alkali:PAN molar ratio | Reaction Temp., °C | time, hr. | GS-HPAN water-insol., acid form Yield, g. | % N |
|---|---|---|---|---|---|---|---|---|
| 1B | 15 | 6.12 | NaOH | 1.3:1 | 92 | 3.0 | — | — |
| 2B | 60 | 3.0 | NaOH | 1.3:1 | 90 | 3.0 | — | — |
| 3B | 50 | 6.25 | NaOH | 1.3:1 | 95 | 3.0 | 37 | 4.2 |
| 4B | 50 | 6.25 | NaOH | 1.3:1 | 95 | 1.5 | 41 | 4.3 |
| 5B | 32 | 3.2 | KOH | 2.7:1 | 100 | 1.5 | — | 5.5 |
| 6B | 33 | 4.4 | KOH | 1:1 | 100 | 2.5 | 32 | — |
| 7B | 10 | 4.0 | KOH | 7.2:1 | 80 | 2.0 | — | 6.5 |
| 8B | 12 | 4.6 | NaOH | 1.3:1 | 92 | 3.0 | — | — |

C. Preparation of water-insoluble GS-HPAN absorbent compositions

To prepare the absorbent polymer, 5 g. of the water-insoluble acid form of GS-HPAN selected from Examples 1B–8B were sifted into 500 ml. of rapidly stirred water, and high-speed stirring was continued for 30 sec. The pH of the dispersion was adjusted to 6–9 by addition of 1N potassium, sodium, or ammonium hydroxide. Some of the resulting viscous solutions were then spread on trays and dried at 25°–35° C. to yield a continuous film of absorbent polymer; others, after tray drying, were coarsely ground to a flake-like material. Still other solutions of the water-soluble GS-HPAN compositions were drum dried using a drum temperature of about 132° C. This product was also coarsely ground.

To rapidly evaluate water absorbency of the dry, particulate products, 0.25 g. of the now water-insoluble GS-HPAN absorbent polymer was sifted into 500 ml. of distilled water and allowed to soak for 30 min. The mixture, containing swollen polymer and excess water, was then poured onto a 40-mesh sieve held in a funnel leading to a graduated cylinder. The unabsorbed water was collected and measured, and the grams of fluid absorbed per gram of dry polymer were calculated.

A similar procedure was followed to determine the absorption of an electrolyte solution simulating urine (simulated urine: 97.09% distilled water, 1.94% urea, 0.80% NaCl, 0.11% MgSO₄·7H₂O, 0.06% CaCl₂). One gram of absorber is soaked for 30 min. in 100 ml. of simulated urine, poured through a 60-mesh sieve, and the excess urine collected and measured.

The procedure used with 0.9% sodium chloride solution was identical to that used with synthetic urine. See Table 3.

Table 3

| Example | Alkali[1] | Method of drying | Absorbency of insol. GS-HPAN Water, g./g.[2] | Synthetic urine, g./g.[2] | 0.9% NaCl solution, g./g.[2] |
|---|---|---|---|---|---|
| 1C | NaOH | tray | 320 | 34 | — |
| 2C | NaOH | tray | 160 | 30 | — |
| 2C | NaOH | drum | 189 | 34 | — |
| 3C-1 | KOH | drum | 896 | — | 60 |
| 3C-2 | KOH | tray | 648 | 54 | — |
| 3C-3 | NH₄OH | tray | 725 | 53 | — |
| 3C-4 | NaOH | tray | 711 | 61 | — |
| 4C | KOH | drum | 1000 | 60 | — |
| 5C | KOH | tray | 1150 | — | 115 |
| 7C | KOH | tray | 1040 | — | 140 |
| 8C | NaOH | tray | 973 | 74 | — |
| Cellulose (control) | — | — | — | 34 | — |

[1] Alkali used to adjust pH of GS-HPAN.
[2] g./g. = grams of absorbed substance per gram absorbent composition.

EXAMPLE 9

Absorbents for aqueous-organic fluids are prepared by reacting saponified starch-polyacrylonitrile in the acid form with an organic amine.

Ten grams of the acid form of GS-HPAN of Example 3B were sifted into 1 liter of water, and 4 ml. of triethylamine were added to the stirred mixture. The resulting thick dispersion was spread onto a tray and allowed to dry at 25°–35° C. The resulting continuous film was then coarsely ground and tested for absorbency as described in Examples 1-8. One gram of this polymer absorbed 48 g. of simulated urine, 80 g. of 80:20 (by volume) ethanol:water and 87 g of 40:40:20 (by volume) acetone:methanol:water.

EXAMPLE 10

A stirred slurry of 135 g. of wheat starch in 2400 ml. of water was heated for 30 min. at 85°–90° C. and then cooled under a nitrogen atmosphere to 25° C. To the stirred mixture were added 75 g. of 0.1 molar ceric ammonium nitrate solution in 1N nitric acid. After 10 min., 159 g. of flash-distilled acrylonitrile were added and the mixture stirred for 3 hr. at 35° C.

The mixture was diluted with water, sodium hydroxide was added in varied amounts, and the mixture was heated to temperatures of 95°–150° C., Table 4. An autoclave was used for temperatures over 100° C. The resulting water-soluble GS-HPAN compositions were shown by infrared analysis to be substantially the same as the composition prepared in accordance with Examples 1-8.

Table 4

| Conc. of GS-PAN in water, % | NaOH:PAN mole ratio | Reaction temp., °C. | Reaction time, hr. |
|---|---|---|---|
| 4.7 | 0.85:1 | 95 | 3.0 |
| 2.4 | 0.85:1 | 95 | 3.0 |
| 2.4 | 0.6:1 | 95 | 3.0 |
| 2.4 | 0.4:1 | 95 | 3.0 |
| 2.4 | 0.4:1 | 125 | 3.0 |
| 4.7 | 0.2:1 | 150 | 1.5 |
| 6.0 | 0.4:1 | 150 | — |
| 4.7 | 0.1:1 | 150 | — |

EXAMPLE 11

A particularly convenient method of obtaining the absorbent polymer in particulate form is to loosely pack a column with the acid from of GS-HPAN and then pass gaseous ammonia up through the column for 15 min. Infrared analysis shows conversion from the carboxyl to the carboxylate form. See Table 5.

EXAMPLE 12

The wide pH range which may be used to prepare the absorbent polymer is shown in Table 6. The water-insoluble acidic polymer of Example 3B was neutralized with potassium hydroxide to the pH's given in the table and the dispersions then dried and ground as in Example 1C.

EXAMPLE 13

The following procedure illustrates prior isolation of the starch-polyacrylonitrile graft copolymer is unnecessary.

Table 5

| Acid form of GS-HPAN (Example) | Absorbency | | |
|---|---|---|---|
| | Water per polymer, g./g. | Synthetic urine per polymer, g./g. | 0.9% NaCl solution per polymer, g./g. |
| 3B | 1300 | 80 | — |
| 4B | 960 | 52 | 50 |

Table 6

| pH Before drying | Absorbency | |
|---|---|---|
| | Water per polymer, g./g. | 0.9% NaCl solution per polymer, g./g. |
| 4.0 | 450 | — |
| 4.8 | 820 | 60 |
| 6.45 | 960 | 80 |
| 7.85 | 920 | 100 |
| 11.3 | 580 | 80 |
| 12.0 | 340 | 60 |

A slurry of 33.2 g. of waxy corn starch in 600 ml. of distilled water was stirred and heated at 90° C. for 30 min. and then cooled to 25° C. under nitrogen. To the stirred mixture was added 18.7 g. of 0.1 molar ceric ammonium nitrate in 1N nitric acid. After the mixture was stirred for 10 min., 40 g. of acrylonitrile were added. The reaction mixture was stirred for 3 hr. at 35° C. and then heated to 90° C. A solution of 25 g. of sodium hydroxide in 600 ml. of water was added, and stirring at 90° C. was continued for 3 hour. The thick, clear dispersion was diluted to 5% solids and cooled to room temperature. The pH was adjusted to 3.2 by addition of 28g. of sulfuric acid. The acid form of GS-HPAN was separated by centrifugation, washed with 1 liter of water, and finally dewatered with 5:1 methanol:acetone and dried. The yield was 64 g.

The absorbent form of the copolymer (i.e., water-insoluble GS-HPAN) was prepared by neutralizing with potassium hydroxide, tray drying, and coarse grinding as in Examples 1-8. This composition absorbed 795 times its weight of water at 25° C. and 59 times its weight of synthetic urine.

The procedure was repeated with the exception that 37.4 g. of waxy corn starch, 80 g. of acrylonitrile, and 44 g. of NaOH (i.e., 0.75 mole NaOH per mole PAN) were used. The absorbent form, prepared as above, absorbed 1480 times it weight of water and 87 times its weight of synthetic urine.

EXAMPLE 14

The following procedure illustrates the preparation of water-insoluble GS-HPAN with no intermediate isolation steps.

Preparation of the starch-polyacrylonitrile graft copolymer and its reaction with sodium hydroxide were carried out as in Example 13 with 37.4 g. waxy corn starch, 40 g. acrylonitrile, and 25 g. NaOH. The thick, clear dispersion was diluted to 5% solids and drum dried directly without acidification using a drum temperature of 132° C. The yield was 96 g. The dry product was crushed and passed through a coarse screen. This polymer absorbed 280 times its weight of water at 25° C. and 56 times its weight of synthetic urine.

The above procedure was repeated except that the thick, clear dispersion was drum dried at 13% solids and gave a comparable product.

The above procedure was again repeated with the exception that 37.4 g. waxy corn starch, 80 g. acrylonitrile, and 36 g. NaOH (i.e., 0.6 mol. NaOH per mole PAN) were used. The absorbent form, prepared as above, absorbed 425 times it own weight of water and 50 times its weight synthetic urine.

EXAMPLE 15

The rapidity with which these polymer will absorb aqueous fluids is shown in Table 7 for the absorbent composition of Example 3C-2 which was tray dried.

EXAMPLE 16

As an estimate of the absorbency of these polymers under pressure, the compositions of Example 15 containing 648 g./g. water and 54 g./g. urine was centrifuged at 45 and 180 × gravity. It is apparent from Table 8 that this polymer loses only a small percentage of its absorbed fluid under pressure, as compared with cellulose.

EXAMPLE 17

The useful absorptive properties of these polymers are not confined only to synthetic electrolyte solutions or to water.

The composition of Example 3C-2 absorbed 40 times its weight of pork liver blood, 100 times its weight of human urine, more than 300 times its weight of water at 75° C., and more than 300 times its weight of water at 0° C.

EXAMPLE 18

A 2-cm. square of absorbent polymer film, prepared from the tray-dried product of Example 3C-2 weighed 0.03 g. and had a thickness of 0.009 cm. When placed in a tray of distilled water, the film imbibed water immediately, and after 10 min. had swelled to an 11.5-cm. square weighing 9.2 g., which is an absorbence of 300 g./g. When the pH was adjusted to 2.3 with hydrochloric acid, the film shank back to a 2-cm. square and showed rubberlike elasticity. When the surrounding liquid was replaced first with potassium hydroxide solution (pH 11), then with distilled water, and finally with hydrochloric acid solution (pH 2.3), the respective dimensions of the squares were 7.5, 12, and 2 cm. This cycling of expansion and shrinkage with pH adjustment was repeated three times. Each time the dimensional changes were the same, and apparently the film will undergo extensions and contractions repeatedly.

Table 7

| Time, sec. | Absorbency | |
|---|---|---|
| | Water per polymer, g./g. | Synthetic urine per polymer, g./g. |
| 30 | 365 | — |
| 60 | 410 | 39 |
| 180 | 538 | — |
| 300 | 570 | 46 |
| 600 | 616 | 49 |
| 1800 | 648 | 54 |

Table 7-continued

| Time, sec. | Absorbency | |
|---|---|---|
| | Water per polymer, g./g. | Synthetic urine per polymer, g./g. |
| 3600 | — | 54 |

Table 8

| | Fluid per polymer, g./g. | | |
|---|---|---|---|
| | No pressure | 45 × g. | 180 × g. |
| Cellulose fibers | | | |
| Water | 40 | 2.1 | 1.05 |
| Synthetic urine | 32 | 1.8 | 1.0 |
| Polymer of Example 15 | | | |
| Water | 648 | 409 | — |
| Synthetic urine | 54 | 40 | 37 |

EXAMPLE 19

Another useful form of the absorbent copolymer is the sponge-like mat which is obtained when the viscous mixture of Example 4B, after addition of alkali to pH 6–9, is freeze dried. Such a freeze-dried product absorbed more than 400 times its weight in water.

EXAMPLE 20

The following examples show that efficient absorbents for aqueous fluids may be prepared by mixing water-soluble GS-HPAN with inexpensive extenders and drying the resulting mixtures.

Five-gram samples of the water-insoluble acid form of GS-HPAN of Example 3B were sifted into 500 ml. of water and the pH adjusted to 7-9 with potassium hydroxide solution. Dispersions of 5 g. of the extenders in 500 ml. of water were prepared separately. Heat was applied to the extender dispersions when necessary to obtain a smooth dispersion. The two dispersions were mixed and the final dispersion either spread onto a tray and allowed to dry at 25°–35° C. in a forced air oven, or drum dried at about 130°. The resulting continuous film was coarsely ground, Table 9.

EXAMPLE 21

A thinned dispersion is obtained by subjecting dispersions of water-soluble GS-HPAN to high shear conditions, such as sonification, colloid milling, or Waring blending. Excessive shearing will drastically reduce the viscosity of an aqueous dispersion.

Table 9

| Extender | Ratio of GS-HPAN to extender | Method of drying | Absorbency | |
|---|---|---|---|---|
| | | | Water per absorbent, g./g. | Synthetic urine per absorbent, g./g. |
| Flour | 50:50 | drum | 334 | 32 |
| Guar | 50:50 | drum | 373 | 38 |
| Acid-modified flour | 33:67 | drum | 370 | 22 |
| Acid-modified flour | 50:50 | drum | 386 | 28 |
| Guar | 50:50 | tray | 448 | 53 |
| Gelatin | 42:58 | tray | 458 | 34 |
| Hydroxyethyl flour | 50:50 | tray | 444 | 40 |
| Control | 100:0 | tray | 648 | 54 |
| Control | 100:0 | drum | 896 | 60 |

A 1-liter 1% dispersion of water-soluble GS-HPAN from Example 3C-2 was sonified at 20 kHz for about 1 hr. which reduced the viscosity of the dispersion from 30,000 cp. to 30 cp. Films prepared by drying the 30-cp. solution at room temperature are soluble and will dissolve in water giving a viscosity near 30 cp.

The soluble films were irradiated with gamma rays from a Cobalt 60 source for a period of time sufficient to obtain total radiation dosages of from 0 to 4 megarads, which resulted in products which were water insoluble and highly absorbent, Table 10.

Table 10

| Radiation dose, megarad | Absorbency of ground film, water per polymer, g./g. |
|---|---|
| 0 | none (polymer is sol.) |
| 1 | 570 |
| 2 | 245 |
| 3 | 165 |
| 4 | 125 |

Saponified starch-polyacrylonitrile can thus be applied to a substrate in the from of a nonviscous aqueous solution and then converted to the absorber form after drying.

EXAMPLE 22

Soluble films were prepared in the manner described in Example 21 and converted to the insoluble, highly absorbent form by heating in a vacuum oven at 160° C. for from 0 to 150 min., Table 11.

Table 11

| Time at 160° C., min. | Absorbency of ground film, water per polymer g./g. |
|---|---|
| 0 | none (polymer is sol.) |
| 30 | 2000 |
| 60 | 1200 |
| 90 | 700 |
| 120 | 400 |
| 150 | 240 |

EXAMPLE 23

Soluble films were prepared in the manner described in Example 21 and converted to the insoluble, highly absorbent form by merely standing at normal room temperature (25° C.) at a range of relative humidities. After 105 days at room temperature and 43% relative humidity, 90% of the film was still soluble while 10% was converted to an insoluble gel. After 7 days at room temperature and 93% relative humidity, over 70% of the film was an insoluble gel which absorbed 600 g. water per gram of polymer. After 100 days at room temperature and 93% relative humidity, over 90% of the film was an insoluble gel which absorbed 400 g. water per gram of polymer.

EXAMPLE 24

If the insoluble, highly absorbent form GS-HPAN is allowed to swell in water and the swollen polymer subjected to mechanical shear, smooth dispersions are obtained which, on further shearing, are converted to low viscosity solutions.

One part, by weight, of polymer film, prepared from the product of Example 3C-4, was swollen in 99 parts of water and then a 10-ml. sample was subjected to sonification at 20 kHz for 5 min. until a clear solution was obtained with a viscosity of 30 cp. On drying at room temperature, a film was obtained which behaved the same as that of Example 21. This film was converted to the insoluble, highly absorbent form by the methods described in Example 21, 22 or 23.

EXAMPLE 25

Various substrates were slurried in 1% by weight dispersions of water-soluble GS-HPAN prepared as described in Example 3C-4 prior to drying.

The mixtures were dried at 25° to 75° C. in a forced air oven and slurried in 2.5 g. of water per gram of absorbent-coated substrate. The volume of supernatant was measured after the mixture had settled and was subtracted from the original volume to give the volume of water absorbed, Table 12.

EXAMPLE 26

A thin film of GS-HPAN may be dried down onto cellulose or paper to greatly increase its water-holding capacity.

A 1% GS-HPAN dispersion was prepared as described in Example 25. This dispersion (Brookfield viscosity: 2980 c.p.s.) was treated for a total of 12 min. in a Branson Sonifier set at maximum output of ultrasound. This treatment reduced the Brookfield viscosity to 80 c.p.s. and thus gave a dispersion which more rapidly penetrated the substrate. Circles of Whatman No. 1 filter paper were soaked for 30 sec. in the dispersion, the excess dispersion was removed by passing through rolls, and the filter papers were dried at 25° C. in a forced air oven. Water-insoluble (GS-HPAN) content of the dried papers was 1.66%. Papers containing water-insoluble GS-HPAN absorbed 3.27 times their weight of deionized water, as compared with 2.55 for untreated papers.

Table 12

| Substrate | % Water-soluble GS-HPAN on substrate, by wt. | Drying temp., ° C. | Absorption, ml. water/g. substrate | |
|---|---|---|---|---|
| | | | Substrate with absorbent | Substrate with no absorbent |
| Celite | 3.0 | 25 | 2.5 | 1.1[1] |
| Cat litter | 1.0 | 75 | 2.0 | — |
| | 2.0 | 75 | 2.5 | 1.2 |
| Wheat starch | 0.5 | 25 | 1.8 | 1.1 |
| | 1.0 | 25 | 2.1 | 1.1 |
| | 2.0 | 25 | 2.5 | 1.1 |

[1]Approximate value due to incomplete settling.

EXAMPLE 27

Finely divided inorganic substrates coated with a thin film of GS-HPAN are not only good absorbents for animal wastes but also help reduce the accompanying objectionable odors.

A portion of cattle feedlot waste, obtained from a soluble fraction by freeze drying, was dissolved in water to give a 1% solution. Twenty-five milliliters of the resulting waste solution were absorbed into 10 g. of the GS-HPAN treated celite of Example 25. After the mixture had stood in a stoppered bottle for several days, microorganism growth was observed, and the highly objectionable odor was no longer evident. Only a mild, musty odor of mold remained.

EXAMPLE 28

When the water-insoluble GS-HPAN coated starches prepared in Example 25 are heated in water, they show a viscosity rise at a lower temperature than untreated starch. Also, final viscosities after heating at 90° C. are higher than those shown by untreated starch.

These properties are shown by heating 8% by weight water dispersions in a Brabender Amylograph at 75 r.p.m. using a 350-g. cartridge and a heating rate of 1.5° C. per minute. Mixtures were heated from 25° to 90° C. over a 43-min. period, held at 90° C. for 17 min., and then cooled back to 25° over a 43-min. period. Results are shown in Table 13.

EXAMPLE 29

The absorbent polymer films act as metal ion-exchangers.

at 25° C. The mixtures were then poured through a 40-mesh sieve, the filtrate collected, and the percent solids determined, Table 14.

Table 14

| Emulsion or dispersion | | | GS-HPAN | | Standing time, min. | % Solids in filtrate |
|---|---|---|---|---|---|---|
| Description | % Solids | Amount | Wt., g. | Form | | |
| Milk, 2% butterfat | 27.4 | 100 ml. | 1.0 | flakes | 60 | 39.4 |
| Sewage sludge | 3.9 | 50 ml. | 1.0 | flakes | — | —[1] |
| Sewage sludge | 3.9 | 100 ml. | 1.0 | flakes | 40 | —[2] |
| Sewage sludge | 3.9 | 100 ml. | 0.5 | film | 45 | 4.8 |
| Oil in water | 52.3[3] | 100 g. | 0.5 | film | 30 | 57.9[3] |
| Oil in water | 9.5[3] | 100 g. | 0.1 | film | 30 | 12.3[3] |

[1]Became a crumbly solid on addition of GS-HPAN.
[2]Was too thick to filter.
[3]Content of linseed oil.

EXAMPLE 31

Films of GS-HPAN serve as insoluble supports for enzymes, and enzymes are readily covalently bonded to the support.

A 0.25-g. sample of tray-dried film prepared as described in Example 3C-2 was added to 10 ml. of a 5% solution of 1-ethyl-3-(3-dimethylaminopropyl) carbodiimide and 5 ml. of stock H.T-1000 α-amylase solution, prepared by making a 10% solution and then filtering. The film was allowed to swell for 30 min. and 10 ml. of 1% calcium chloride solution were added. The film, which shrank considerably, was transferred to fresh calcium chloride solution and finally to distilled water. Gradual swelling of the film was observed on standing in water for 1 wk. Water was finally decanted off, and the film reshrunk with 1% calcium chloride.

Enzyme activity was tested by reacting the film, containing the bound enzyme, with a 1% starch solution in 1% calcium chloride. The film was placed in a Petri dish and 10 ml. of the starch solution added. Incubation was for 1 hr. at 40° C., and iodine solution was used to Table 13

| % H-SPAN on starch | Mixture shows measurable viscosity | | Viscosity at 90° C., Brabender units | Viscosity at end of run, 25° C., Brabender units |
|---|---|---|---|---|
| | Minutes | Temp., °C. | | |
| 0.0 (control) | 36 | 79 | 550 | 2280 |
| 0.5 | 25 | 62 | 950 | 2930 |
| 1.0 | 22 | 58 | 1600 | 2980 |
| 2.0 | 20 | 55 | 2480 | 3930 |

A 20.5-mg. sample of dry film prepared as described in Example 3C-2 was placed into 100 ml. of tap water for 10 min., after which the unabsorbed water was removed and reserved. The water-soaked film was then placed in a second 100 ml. volume of tap water for 1 hr., after which the water was again removed and reserved. This procedure was repeated once more leaving the film to soak for 3 hr. The reserved water and the film were analyzed for K$^+$ and Mg$^+$ by atomic absorption. The water lost 0.068 mmoles of Mg$^{+2}$ and gained 0.066 mmoles of K$^+$.

EXAMPLE 30

This example shows the utility of absorbent polymers prepared in accordance with the invention for concentrating of dewatering aqueous emulsions or dispersions.

Portions of the dried absorbent product of Example 3C-2 were added as ground flakes or as film to various emulsions which were then stirred and allowed to stand test for unreacted starch. The solution was then tested for reducing sugar by the ferricyanide procedure.

The film was then washed with 1% calcium chloride solution, and the procedure was repeated with a fresh starch solution. The procedure was performed a total of three times, and the results are shown in Table 15.

Table 15

| Trial | Starch-iodine color | Reducing sugar, (as glucose), mg. per 100 ml. |
|---|---|---|
| 1 | colorless | 114 |
| 2 | colorless | 121 |
| 3 | slight blue | 78 |

EXAMPLE 32

Enzymes may be rendered insoluble by entrapment in swollen water-insoluble films of GS-HPAN. A 0.25- g. sample of tray-dried film, prepared as described in Example 3C-2, was swollen in 10 ml. of water containing glucoamylase enzyme having approximately 160 glucoamylase units. The film absorbed all of the solution. A 10-ml. portion of 1% calcium chloride solution was added to shrink the film, and the resulting film was then washed several times to remove untrapped enzyme.

Activity of the film was tested by placing it in a Petri dish and adding 5 ml. of a 1% starch solution in 1% calcium chloride at pH 6.5. Five different starch solutions were used consecutively, and after incubation, solutions were tested for reducing sugar by the ferricyanide procedure, Table 16.

Table 16

| Trial | Reducing sugar, (as glucose), mg. per 100 ml. |
|---|---|
| 1 | 288 |
| 2 | 214 |
| 4 | 340 |
| 5 | 520 |

EXAMPLE 33

Addition of the absorbent polymer to soil decreases water loss due to evaporation.

Three grams of water-insoluble GS-HPAN, prepared as described in Example 3C-2, were blended with 300 g. of white sand in a small container (weight: 17 g.) and five bean seeds were planted. Similar plantings were made in sand containing 3.0 g., 1.5 g., 0.75 g., and 0 g. of absorbent polymer. Water was added to each container to bring the total weight to 400 g. Containers were allowed to stand at room temperature overnight, weighed to determine water content, and water was added on the 2nd, 5th, 6th, 7th, and 9th days to bring the total weight to 400 g. Percentages of the original water remaining after standing are shown in Table 17. A high percentage of all the bean seeds germinated.

Table 17

| Day | Days standing without adding water | % Original water remaining Grams absorbent polymer per 300 g. sand | | | |
|---|---|---|---|---|---|
| | | 0 | 0.75 | 1.5 | 3.0 |
| 1 | 0 | 100 | 100 | 100 | 100 |
| 2 | 1 | 63 | 68 | 70 | 70 |
| 5 | 3 | 0 | 11 | 10 | 9 |
| 6 | 1 | 65 | 67 | 65 | 64 |
| 7 | 1 | 60 | 65 | 69 | 68 |
| 8 | 1 | 63 | 66 | 70 | 70 |
| 9 | 2 | 26 | 46 | 49 | 47 |
| 12 | 3 | 10 | 29 | 28 | 29 |

EXAMPLE 34

When dispersions of water-soluble GS-HPAN are added to soil, they act as soil conditioners to stabilize small dirt clods against disintegration in heavy rains, and thus minimize excessive soil packing and the resulting problems of water runoff.

One hundred grams of Miami silt loam were wetted with a combination of 1 ml. of 1% calcium acetate and 30 ml. of a 3% dispersion of water-soluble GS-HPAN, prepared as described in Example 25. Using a method for evaluating soil conditioners described by R. M. Hedrick [J. Agr. Food Chem. 2: 182 (1954)], the wet cake was pressed through a screen with 4.76-mm. openings, and the resulting crumbs were dried in a forced air oven at 60° C. Forty grams of the dry crumb were placed on a 20-mesh sieve which was then agitated gently in water for 30 min. At the end of this time, over 96% of the crumb was retained on the sieve, as compared to 0% for a control crumb which was prepared in the absence of polymer.

When the experiment was repeated with 30 ml. of a 0.09% dispersion of water-soluble GS-HPAN, 20% of the crumbs was retained on the 40-mesh screen. The remainder passed through.

EXAMPLE 35

When seeds are slurried in a dispersion of water-soluble GS-HPAN and the resulting slurry spread in a tray and allowed to dry, a continuous film of insoluble GS-HPAN containing entrapped seeds is obtained. This system is ideally suited to hydroponic gardening, since addition of an aqueous nutrient solution to the film yields a highly swollen gel containing entrapped and completely immobilized seeds.

A 1% saponified starch-polyacrylonitrile dispersion was prepared from the product of Example 3B by adding potassium hydroxide to pH 6–9. Marigold seeds were added, and the resulting dispersion was spread onto a tray and allowed to dry at room temperature. A hydroponic nutrient mixture was prepared from the following components: potassium nitrate (16.49%), ammonium sulfate (4.80%, potassium sulfate (42.22%, calcium dehydrogen phosphate (14.44%, calcium sulfate (16.06%), magnesium sulfate (5.98%). One tablespoon of this mixture was dissolved in 1 gal. of water, and the resulting solution was added to the film containing the entrapped seeds. Swelling of the film was observed, and the seeds germinated.

This experiment was repeated with petunia seeds, and germination of the seeds was again observed.

We claim:
1. Aqueous fluid-absorbing compositions comprising water-insoluble alkali salts of aqueous alkali saponified gelatinized-starch-polyacrylonitrile graft polymers containing gelatinized starch (GS) and saponified polyacrylonitrile (HPAN) in molar ratios of from about 1:1.5 to 1:9 GS:HPAN, said water-insoluble alkali salts of aqueous alkali saponified gelatinized-starch-polyacrylonitrile graft polymers being further characterized as water-insoluble solids capable of absorbing in excess of 300 parts of water by weight per part of said water-insoluble solids.

2. Aqueous fluid-absorbing compositions as described in claim 1 wherein the insoluble alkali salts of aqueous alkali saponified gelatinized-starch-polyacrylonitrile graft polymers are further characterized as water-insoluble solids capable of absorbing from about 300 to 1500 parts by weight per part of said water-insoluble solids.

3. Aqueous fluid-absorbing compositions as described in claim 1 wherein the gelatinized starch contained therein is wheat starch, corn starch, waxy corn starch, or waxy sorghum starch.

4. A method of preparing water-insoluble aqueous fluid-absorbing compositions comprising the following steps:
   a. saponifying a gelatinized-starch-polyacrylonitrile graft polymer (GS-PAN) in an aqueous slurry with an alkali in amounts such that the molar ratio of alkali to the acrylonitrile repeating unit of said GS-PAN is from about 0.1:1 to 7:1 to form a water-soluble saponified GS-PAN (water-soluble GS-HPAN); and b. optionally adjusting the pH of said water-soluble GS-HPAN to about 3, followed by isolating the resulting water-insoluble acid form of GS-HPAN, and readjusting the pH of said water-insoluble acid form of GS-HPAN to from about 4 to 12 to reform said water-soluble GS-HPAN; and c. drying said water-soluble GS-HPAN to a moisture level of from about 1 to 15% water by weight.

5. A method of preparing water-insoluble aqueous fluid-absorbing compositions as described in claim 4 wherein the molar ratio of alkali to the acrylonitrile repeating unit of said GS-PAN is from about 0.6:1 to 7:1.

6. A method of preparing water-insoluble aqueous fluid-absorbing compositions as described in claim 4 wherein the GS-PAN is prepared by the method comprising the steps of:
   a. gelatinizing starch (GS) in an aqueous suspension at a temperature of from 80° to 100° C. for at least 15 min.; and
   b. graft polymerizing the gelatinized starch resulting from step (a) with acrylonitrile (AN) or methacrylonitrile (MAN) in amounts such that the molar ratio of GS to AN or MAN is from about 1:1.5 to 1:9, said graft polymerizing taking place in the presence of a suitable polymerization initiator.

7. A method of preparing water-insoluble aqueous fluid-absorbing compositions as described in claim 6 wherein the starch is wheat starch, corn starch, waxy corn starch, or waxy sorghum starch.

8. A method of preparing insoluble aqueous-organic fluid-absorbing compositions comprising the steps of:
   a. saponifying a gelatinized-starch-polyacrylonitrile graft polymer (GS-PAN) in an aqueous slurry with an alkali in amounts such that the molar ratio of alkali to acrylonitrile repeating units of said GS-PAN is from about 0.1:1 to 7:1 to form a water-soluble saponified GS-PAN (water-soluble GS-HPAN);
   b. adjusting the pH of said water-soluble GS-HPAN to about 3, followed by isolating the resulting water-insoluble acid form of GS-HPAN;
   c. reacting said water-insoluble acid form of GS-HPAN in an aqueous slurry with an organic amine in amounts such that the pH of the reaction mixture is from 5 to 11; and
   d. drying the product of step (c) to a moisture content of about 1 to 15% water by weight.

9. A method of preparing insoluble aqueous-organic fluid-absorbing compositions as described in claim 8 wherein the organic amine is methyl-, ethyl-, hexyl-, dodecyl-, benzyl-, chlorobenzyl-, or ethanolamine, secondary or tertiary analogs of the same, aniline, cyclohexylamine, or pyridine.

10. A method of preparing a low viscosity aqueous dispersion of a water-soluble saponified gelatinized-starch-polyacrylonitrile graft polymer capable of forming a water-insoluble aqueous, fluid-absorbing composition comprising the steps of:
    a. saponifying a gelatinized-starch-polyacrylonitrile graft polymer (GS-PAN) in an aqueous slurry with an alkali in amounts such that the molar ratio of alkali to the acrylonitrile repeating unit of said GS-PAN is from about 0.0:1 to 7:1 to form a water-soluble saponified GS-PAN (water-soluble GS-HPAN); and
    b. optionally adjusting the pH of said water-soluble GS-HPAN to about 3, followed by isolating the resulting water-insoluble acid form of GS-HPAN, and readjusting the pH of said water-insoluble acid form of GS-HPAN to form about 4 to 12 to reform said water-soluble GS-HPAN; and
    c. sonifying a 1% by weight aqueous dispersion of said water-soluble GS-HPAN at a sonifying frequency and for a time sufficient to reduce the viscosity of said dispersion to about 30 cp.

11. A method of preparing water-insoluble aqueous fluid-absorbing compositions comprising drying a low viscosity aqueous dispersion of a water-soluble saponified gelatinized-starch-polyacrylonitrile graft polymer prepared as described in claim 10 at a temperature of about 160° C. for from about 15 to 120 min.

12. A method of preparing water-insoluble aqueous fluid-absorbing compositions comprising drying a low viscosity aqueous dispersion of a water-soluble saponified gelatinized-starch-polyacrylonitrile graft polymer prepared as described in claim 10 at a temperature of about 25° C. for from about 7 days in a humid atmosphere having about 90% relative humidity to about 100 days in a humid atmosphere having from 43 to 90% relative humidity.

13. A method of increasing the water absorbency of water-insoluble substrates comprising the steps of:
    a. saponifying a gelatinized-starch-polyacrylonitrile graft polymer (GS-PAN) in an aqueous slurry with an alkali in amounts such that the molar ratio of alkali to the acrylonitrile repeating unit of said GS-PAN is from about 0.1:1 to 7:1 to form a water-soluble saponified GS-PAN (water-soluble GS-HPAN); and
    b. optionally adjusting the pH of said water-soluble GS-HPAN to about 3, followed by isolating the resulting water-insoluble acid form of GS-HPAN, and readjusting the pH of said water-insoluble acid form of GS-HPAN to from about 4 to 12 to reform said water-soluble GS-HPAN; and
    c. mixing said water-soluble GS-HPAN in an aqueous slurry of a water-insoluble substrate; and
    d. drying the mixture resulting from step (c) to a moisture content of 1 to 15% water by weight.

14. A method of increasing the water absorbency of water-insoluble substrates as described in claim 13 wherein the water-insoluble substrate is diatomaceous silica, clay, animal litter or bedding, granular starch, cellulose fibers, paper, or cloth.

15. Water-absorbent substrates prepared as described in claim 14.

* * * * *